United States Patent [19]

Sasisekharan et al.

[11] Patent Number: 5,830,726
[45] Date of Patent: Nov. 3, 1998

[54] METHOD FOR OBTAINING A MODIFIED HEPARINASE GENE

[75] Inventors: Ramnath Sasisekharan, Arlington, Mass.; Kelley Moremen, Athens, Ga.; Charles I. Cooney, Brookline, Mass.; Joseph J. Zimmermann, Elm Grove, Wis.; Robert S. Langer, Newton, Mass.

[73] Assignee: Massachusetts Institute of Technology, Cambridge, Mass.

[21] Appl. No.: 445,342

[22] Filed: May 19, 1995

Related U.S. Application Data

[62] Division of Ser. No. 783,706, Oct. 23, 1991, Pat. No. 5,714,376.

[51] Int. Cl.$^6$ .......................... C12N 15/10; C12N 15/60; C12N 9/88
[52] U.S. Cl. ................... 435/172.3; 536/23.2; 435/232; 435/252.3; 435/252.33; 435/320.1
[58] Field of Search .......................... 536/23.2; 435/232, 435/252.3, 252.33, 320.1, 172.3

[56] References Cited

U.S. PATENT DOCUMENTS

| | | | |
|---|---|---|---|
| 4,757,012 | 7/1988 | Estell et al. | 435/172.3 |
| 4,839,293 | 6/1989 | Cantor et al. | 435/320.1 |

OTHER PUBLICATIONS

V.C. Yang et al., "Purification and Characterization of Heparinase From Flavobacterium heparinum", J. Biol. Chem. 260(3): 1849–1857, Feb. 1985.

S.L. Berger et al. (eds.) "Guide to Molecular Cloning Techniques", Meth. Enzymol. 152: 393–399, 415–423, 432–447, 661–704, 1987.

M.P. Deutscher (ed), "Guide to Protein Purification", Meth. Enzymol. 182: 602–613, 738–751, 1991.

*Primary Examiner*—Rebecca E. Prouty
*Attorney, Agent, or Firm*—Arnall Golden & Gregory, LLP

[57] ABSTRACT

The cloning of the heparinase gene from *Flavobacterium Heparinum* using the polymerase chain reaction is described. The Open Reading Frame (ORF) corresponded to 1152 base pairs encoding a precursor protein of MW 43,800 daltons. The amino acid sequence reveals a 20-residue leader peptide. The gene was expressed in two expression systems in *E. coli*.

3 Claims, 2 Drawing Sheets

FIG. 3

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 1379
        ( B ) TYPE: nucleic acid
        ( C ) STRANDEDNESS: single
        ( D ) TOPOLOGY: linear     ( x i ) SEQUENCE DESCRIPTION: SEQ ID NO:1:

```
CCTTTTGGGA  GCAAAGGCAG  AACCATCTCC  GAACAAAGGC  AGAACCAGCC  TGTAAACAGA      60

CAGCAATTCA  TCCGCTTTCA  ACCAAAGTGA  AAGCATTTAA  TACAATACCA  GAATGTCGCA     120

TTTCCCTTTC  AGCGTACTTT  TTGGGTAAAT  AACCAATAAA  AACTAAAGAC  GGATGAAAAA     180

ACAAATTCTA  TATCTGATTG  TACTTCAGCA  ACTGTTCCTC  TGTTCGGCTT  ACGCCAGCA      240
```

-continued

| | | | | | |
|---|---|---|---|---|---|
| AAAAAAATCC | GGTAACATCC | CTTACCGGGT | AAATGTGCAG | GCCGACAGTG | CTAAGCAGAA | 300
| GGCGATTATT | GACAACAAAT | GGGTGGCAGT | AGGCATCAAT | AAACCTTATG | CATTACAATA | 360
| TGACGATAAA | CTGCGCTTTA | ATGGAAAACC | ATCCTATCGC | TTTGAGCTTA | AAGCCGAAGA | 420
| CAATTCGCTT | GAAGGTTATG | CTGCAGGAGA | AACAAAGGGC | CGTACAGAAT | TGTCGTACAG | 480
| CTATGCAACC | ACCAATGATT | TTAAGAAATT | TCCCCCAAGC | GTATACCAAA | ATGCGCAAAA | 540
| GCTAAAAACC | GTTTATCATT | ACGGCAAAGG | GATTTGTGAA | CAGGGGAGCT | CCCGCAGCTA | 600
| TACCTTTTCA | GTGTACATAC | CCTCCTCCTT | CCCCGACAAT | GCGACTACTA | TTTTTGCCCA | 660
| ATGGCATGGT | CGACCCAGCA | GAACGCTTGT | AGCTACACCA | GAGGGAGAAA | TTAAAACACT | 720
| GAGCATAGAA | GAGTTTTTGG | CCTTATACGA | CCGCATGATC | TTCAAAAAAA | ATATCGCCCA | 780
| TGATAAAGTT | GAAAAAAAAG | ATAAGGACGG | AAAAATTACT | TATGTAGCCG | AAAGCCAAA | 840
| TGGCTGGAAG | GTAGAACAAG | GTGGTTATCC | CACGCTGGCC | TTTGGTTTTT | CTAAAGGGTA | 900
| TTTTTACATC | AAGGCAAACT | CCGACCGGCA | GTGGCTTACC | GACAAGCCG | ACCGTAACAA | 960
| TGCCAATCCC | GAGAATAGTG | AAGTAATGAA | GCCCTATTCC | TCGGAATACA | AAACTTCAAC | 1020
| CATTGCCTAT | AAAATGCCCT | TTGCCCAGTT | CCCTAAAGAT | TGCTGGATTA | CTTTTGATGT | 1080
| CGCCATAGAC | TGGACGAAAT | ATGGAAAAGA | GGCCAATACA | ATTTGAAAC | CCGGTAAGCT | 1140
| GGATGTGATG | ATGACTTATA | CCAAGAATAA | GAAACCACAA | AAAGCGCATA | TCGTAAACCA | 1200
| GCAGGAAATC | CTGATCGGAC | GTAACGATGA | CGATGGCTAT | TACTTCAAAT | TTGGAATTTA | 1260
| CAGGGTCGGT | AACAGCACGG | TCCCGGTTAC | TTATAACCTG | AGCGGGTACA | GCGAAACTGC | 1320
| CAGATAGCAA | AAGCCCTAAG | CGCATCCGAT | AGGGCTTTTC | TTATATTTAC | AATAAAATT | 1379

( 2 ) INFORMATION FOR SEQ ID NO:2:

( i ) SEQUENCE CHARACTERISTICS:
        ( A ) LENGTH: 384 amino acids
        ( B ) TYPE: amino acid
        ( C ) STRANDEDNESS: single
        ( D ) TOPOLOGY: linear     ( x i ) SEQUENCE DESCRIPTION: SEQ ID NO:2:

| Met | Lys | Lys | Gln | Ile | Leu | Tyr | Leu | Ile | Val | Leu | Gln | Gln | Leu | Phe | Leu |
|---|---|---|---|---|---|---|---|---|---|---|---|---|---|---|---|
| 1 | | | | 5 | | | | | 10 | | | | | 15 | |
| Cys | Ser | Ala | Tyr | Ala | Gln | Gln | Lys | Lys | Ser | Gly | Asn | Ile | Pro | Tyr | Arg |
| | | | 20 | | | | | 25 | | | | | 30 | | |
| Val | Asn | Val | Gln | Ala | Asp | Ser | Ala | Lys | Gln | Lys | Ala | Ile | Ile | Asp | Asn |
| | | 35 | | | | | 40 | | | | | 45 | | | |
| Lys | Trp | Val | Ala | Val | Gly | Ile | Asn | Lys | Pro | Tyr | Ala | Leu | Gln | Tyr | Asp |
| | 50 | | | | | 55 | | | | | 60 | | | | |
| Asp | Lys | Leu | Arg | Phe | Asn | Gly | Lys | Pro | Ser | Tyr | Arg | Phe | Glu | Leu | Lys |
| 65 | | | | | 70 | | | | | 75 | | | | | 80 |
| Ala | Glu | Asp | Asn | Ser | Leu | Glu | Gly | Tyr | Ala | Ala | Gly | Glu | Thr | Lys | Gly |
| | | | | 85 | | | | | 90 | | | | | 95 | |
| Arg | Thr | Glu | Leu | Ser | Tyr | Ser | Tyr | Ala | Thr | Thr | Asn | Asp | Phe | Lys | Lys |
| | | | | 100 | | | | | 105 | | | | | 110 | |
| Phe | Pro | Pro | Ser | Val | Tyr | Gln | Asn | Ala | Gln | Lys | Leu | Lys | Thr | Val | Tyr |
| | | | 115 | | | | | 120 | | | | | 125 | | |
| His | Tyr | Gly | Lys | Gly | Ile | Cys | Glu | Gln | Gly | Ser | Ser | Arg | Ser | Tyr | Thr |
| | | | 130 | | | | | 135 | | | | | 140 | | |
| Phe | Ser | Val | Tyr | Ile | Pro | Ser | Ser | Phe | Pro | Asp | Asn | Ala | Thr | Thr | Ile |
| 145 | | | | | 150 | | | | | 155 | | | | | 160 |
| Phe | Ala | Gln | Trp | His | Gly | Ala | Pro | Ser | Arg | Thr | Leu | Val | Ala | Thr | Pro |

|     |     |     |     | 165 |     |     |     |     | 170 |     |     |     |     | 175 |
|-----|-----|-----|-----|-----|-----|-----|-----|-----|-----|-----|-----|-----|-----|-----|
| Glu | Gly | Glu | Ile | Lys | Thr | Leu | Ser | Ile | Glu | Phe | Leu | Ala | Leu | Tyr |
|     |     |     | 180 |     |     |     |     | 185 |     |     |     | 190 |     |     |
| Asp | Arg | Met | Ile | Phe | Lys | Lys | Asn | Ile | Ala | His | Asp | Lys | Val | Glu | Lys |
|     |     | 195 |     |     |     | 200 |     |     |     |     | 205 |     |     |     |
| Lys | Asp | Lys | Asp | Gly | Lys | Ile | Thr | Tyr | Val | Ala | Gly | Lys | Pro | Asn | Gly |
|     | 210 |     |     |     |     | 215 |     |     |     |     | 220 |     |     |     |
| Trp | Lys | Val | Glu | Gln | Gly | Gly | Tyr | Pro | Thr | Leu | Ala | Phe | Gly | Phe | Ser |
| 225 |     |     |     |     | 230 |     |     |     |     | 235 |     |     |     |     | 240 |
| Lys | Gly | Tyr | Phe | Tyr | Ile | Lys | Ala | Asn | Ser | Asp | Arg | Gln | Trp | Leu | Thr |
|     |     |     |     | 245 |     |     |     |     | 250 |     |     |     |     | 255 |     |
| Asp | Lys | Ala | Asp | Arg | Asn | Asn | Ala | Asn | Pro | Glu | Asn | Ser | Glu | Val | Met |
|     |     |     |     | 260 |     |     |     |     | 265 |     |     |     |     | 270 |     |
| Lys | Pro | Tyr | Ser | Ser | Glu | Tyr | Lys | Thr | Ser | Thr | Ile | Ala | Tyr | Lys | Met |
|     |     | 275 |     |     |     |     | 280 |     |     |     |     | 285 |     |     |     |
| Pro | Phe | Ala | Gln | Phe | Pro | Lys | Asp | Cys | Trp | Ile | Thr | Phe | Asp | Val | Ala |
|     | 290 |     |     |     |     | 295 |     |     |     |     | 300 |     |     |     |     |
| Ile | Asp | Trp | Thr | Lys | Tyr | Gly | Lys | Glu | Ala | Asn | Thr | Ile | Leu | Lys | Pro |
| 305 |     |     |     |     | 310 |     |     |     |     | 315 |     |     |     |     | 320 |
| Gly | Lys | Leu | Asp | Val | Met | Met | Thr | Tyr | Thr | Lys | Asn | Lys | Lys | Pro | Gln |
|     |     |     |     | 325 |     |     |     |     | 330 |     |     |     |     | 335 |     |
| Lys | Ala | His | Ile | Val | Asn | Gln | Gln | Glu | Ile | Leu | Ile | Gly | Arg | Asn | Asp |
|     |     |     | 340 |     |     |     |     | 345 |     |     |     |     | 350 |     |     |
| Asp | Asp | Gly | Tyr | Tyr | Phe | Lys | Phe | Gly | Ile | Tyr | Arg | Val | Gly | Asn | Ser |
|     |     | 355 |     |     |     |     | 340 |     |     |     |     | 345 |     |     |     |
| Thr | Val | Pro | Val | Thr | Tyr | Asn | Leu | Ser | Gly | Tyr | Ser | Glu | Thr | Ala | Arg |
|     | 370 |     |     |     |     | 375 |     |     |     |     | 380 |     |     |     |     |

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( i x ) FEATURE:
        ( D ) OTHER INFORMATION: "Xaa represents either lysine or
           arginine residues wherein trypsin cuts."

( x i ) SEQUENCE DESCRIPTION: SEQ ID NO:3:

| Xaa | Gly | Ile | Cys | Glu | Gln | Gly | Ser | Ser | Arg |
|-----|-----|-----|-----|-----|-----|-----|-----|-----|-----|
| 1   |     |     |     | 5   |     |     |     |     | 10  |

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear     ( i x ) FEATURE:
        ( D ) OTHER INFORMATION: "Xaa represents either lysine or
           arginine residues wherein trypsin cuts."

( x i ) SEQUENCE DESCRIPTION: SEQ ID NO:4:

| Xaa | Thr | Val | Tyr | His | Tyr | Gly | Lys |
|-----|-----|-----|-----|-----|-----|-----|-----|
| 1   |     |     |     | 5   |     |     |     |

( 2 ) INFORMATION FOR SEQ ID NO:5:

( i ) SEQUENCE CHARACTERISTICS:
: ( A ) LENGTH: 8 amino acids
: ( B ) TYPE: amino acid
: ( C ) STRANDEDNESS: single
: ( D ) TOPOLOGY: linear ( i x ) FEATURE:
: ( D ) OTHER INFORMATION: "Xaa represents either lysine or arginine residues wherein trypsin cuts."

( x i ) SEQUENCE DESCRIPTION: SEQ ID NO:5:

```
Xaa  Thr  Ser  Thr  Ile  Ala  Tyr  Lys
1                 5
```

( 2 ) INFORMATION FOR SEQ ID NO:6:

: ( i ) SEQUENCE CHARACTERISTICS:
:: ( A ) LENGTH: 6 amino acids
:: ( B ) TYPE: amino acid
:: ( C ) STRANDEDNESS: single
:: ( D ) TOPOLOGY: linear : ( i x ) FEATURE:
:: ( D ) OTHER INFORMATION: "Xaa represents either lysine or arginine residues wherein trypsin cuts."

: ( x i ) SEQUENCE DESCRIPTION: SEQ ID NO:6:

```
Xaa  Phe  Gly  Ile  Tyr  Arg
1                 5
```

( 2 ) INFORMATION FOR SEQ ID NO:7:

: ( i ) SEQUENCE CHARACTERISTICS:
:: ( A ) LENGTH: 22 amino acids
:: ( B ) TYPE: amino acid
:: ( C ) STRANDEDNESS: single
:: ( D ) TOPOLOGY: linear : ( i x ) FEATURE:
:: ( D ) OTHER INFORMATION: "Xaa at position 1 represents either lysine or arginine residues wherein trypsin cuts, and Xaa at position 17 represents undetermined."

: ( x i ) SEQUENCE DESCRIPTION: SEQ ID NO:7:

```
Xaa  Ala  Asp  Ile  Val  Asn  Gln  Gln  Glu  Ile  Leu  Ile  Gly  Arg  Asp  Asp
1                 5                           10                          15
Xaa  Gly  Tyr  Tyr  Phe  Lys
             20
```

( 2 ) INFORMATION FOR SEQ ID NO:8:

: ( i ) SEQUENCE CHARACTERISTICS:
:: ( A ) LENGTH: 25 amino acids
:: ( B ) TYPE: amino acid
:: ( C ) STRANDEDNESS: single
:: ( D ) TOPOLOGY: linear : ( i x ) FEATURE:
:: ( D ) OTHER INFORMATION: "Xaa at position 1 represents either lysine or arginine residues wherein trypsin cuts, and Xaa at position 25 represents undetermined."

: ( x i ) SEQUENCE DESCRIPTION: SEQ ID NO:8:

```
Xaa  Ile  Thr  Tyr  Val  Ala  Gly  Lys  Pro  Asn  Gly  Asn  Lys  Val  Glu  Gln
1                 5                           10                          15
Gly  Gly  Tyr  Pro  Thr  Leu  Ala  Phe  Xaa
              20                         25
```

( 2 ) INFORMATION FOR SEQ ID NO:9:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( i x ) FEATURE:
    ( D ) OTHER INFORMATION: "Xaa at position 1 represents either
    lysine or arginine residues wherein trypsin cuts, and
    Xaa at position 21 represents undetermined."

( x i ) SEQUENCE DESCRIPTION: SEQ ID NO:9:

```
Xaa Met Pro Phe Ala Gln Phe Pro Lys Asp Cys Trp Ile Thr Phe Asp
1               5                   10                  15
Val Ala Ile Asp Xaa Thr Lys
            20
```

( 2 ) INFORMATION FOR SEQ ID NO:10:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear     ( i x ) FEATURE:
        ( D ) OTHER INFORMATION: "Xaa at position 1 represents either
        lysine or arginine residues wherein trypsin cuts."

( x i ) SEQUENCE DESCRIPTION: SEQ ID NO:10:

```
Xaa Asn Leu Ser Gly Tyr Ser Glu Thr Ala Arg
1               5                   10
```

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear     ( x i ) SEQUENCE DESCRIPTION: SEQ ID NO:11:

```
Lys Asn Ile Ala His Asp Lys Val Glu Lys Lys
1               5                   10
```

( 2 ) INFORMATION FOR SEQ ID NO:12:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear     ( x i ) SEQUENCE DESCRIPTION: SEQ ID NO:12:

```
Lys Thr Leu Ser Ile Glu Glu Phe Leu Ala Leu Tyr Asp Arg
1               5                   10
```

( 2 ) INFORMATION FOR SEQ ID NO:13:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear     ( x i ) SEQUENCE DESCRIPTION: SEQ ID NO:13:

```
Arg Ser Tyr Thr Phe Ser Val Tyr Ile Pro Ser Ser Phe Pro Asp Asn
1               5                   10                  15
Ala Thr Thr Ile Phe Ala Gln Trp His Gly Ala Pro Ser Arg Thr Leu
```

```
                    20                   25                  30
Val  Thr  Phe  Glu  Ile  Lys
               35
```

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear     ( i x ) FEATURE:
        ( D ) OTHER INFORMATION: "N at position 6 is inosine, N at
            position 12 is a T or a C, and N at positions 15 and
            18 are an A or a G."

( x i ) SEQUENCE DESCRIPTION: SEQ ID NO:14:

```
AAAGGNATHT  GNGANCANGG                                                      20
```

( 2 ) INFORMATION FOR SEQ ID NO:15:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: linear     ( i x ) FEATURE:
        ( D ) OTHER INFORMATION: "N at position 6 and 21 is inosine,
            N at position 9, 18 and 27 is a T or a C, and N at
            positions 15 and 24 are an A or a G."

( x i ) SEQUENCE DESCRIPTION: SEQ ID NO:15:

```
ATGCCNTTNG  CNCANTTNCC  NAANGANGA                                           29
```

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: double
        ( D ) TOPOLOGY: linear     ( i x ) FEATURE:
        ( D ) OTHER INFORMATION: "N at position 3, 15 and 18 is
            inosine, N at position 6 and 18 is a T or a C, and N
            at positions 9 and 12 are an A or a G."

( x i ) SEQUENCE DESCRIPTION: SEQ ID NO:16:

```
ATNAANCANG  ANATNNTNAT  HGG                                                 23
```

( 2 ) INFORMATION FOR SEQ ID NO:17:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear     ( x i ) SEQUENCE DESCRIPTION: SEQ ID NO:17:

```
Gly  Ile  Gln  Lys
 1
```

( 2 ) INFORMATION FOR SEQ ID NO:18:

( i ) SEQUENCE CHARACTERISTICS:
        ( A ) LENGTH: 12
        ( B ) TYPE: nucleic acid
        ( C ) STRANDEDNESS: double -continued ( D ) TOPOLOGY: linear ( x i ) SEQUENCE DESCRIPTION: SEQ ID NO:18:

GGAATTCAGA AA 12

( 2 ) INFORMATION FOR SEQ ID NO:19:

( i ) SEQUENCE CHARACTERISTICS:
( A ) LENGTH: 18
( B ) TYPE: nucleic acid
( C ) STRANDEDNESS: double
( D ) TOPOLOGY: linear ( x i ) SEQUENCE DESCRIPTION: SEQ ID NO:19:

ACTGCCAGAT AGGGATCC 18

( 2 ) INFORMATION FOR SEQ ID NO:20:

( i ) SEQUENCE CHARACTERISTICS:
( A ) LENGTH: 18
( B ) TYPE: nucleic acid
( C ) STRANDEDNESS: double
( D ) TOPOLOGY: linear ( x i ) SEQUENCE DESCRIPTION: SEQ ID NO:20:

TAACCCGGGA TGAAAAAA 18

( 2 ) INFORMATION FOR SEQ ID NO:21:

( i ) SEQUENCE CHARACTERISTICS:
( A ) LENGTH: 18
( B ) TYPE: nucleic acid
( C ) STRANDEDNESS: double
( D ) TOPOLOGY: linear ( x i ) SEQUENCE DESCRIPTION: SEQ ID NO:21:

GCCAGATAGA AGCTTCCG 18

METHOD FOR OBTAINING A MODIFIED HEPARINASE GENE

This is a divisional of U.S. Ser. No. 07/783,706 filed on Oct. 23, 1991, now U.S. Pat. No. 5,714,376 by Ramnath Sasisekharan, Kelley Moremen, Charles L. Cooney, Joseph J. Zimmermann, and Robert S. Langer entitled "Heparinase Gene from *Flavobacterium heparinum.*"

BACKGROUND OF THE INVENTION

This invention is generally in the area of heparinases and is specifically directed to the gene encoding heparinase I, expressed in *Flavobacterium heparinum.*

The United States government has rights in this invention by virtue of grant number 25810 from the National Institutes of Health.

Heparin is an anticoagulant that activates serine protease inhibitors (serpins), which play a key role in the blood clotting cascade, as described by Damus et al., *Nature* 246:355–357 (1973). According to Lindahl et al., *Trends Biochem. Sci.* 11:221–225 (1986), heparin is the most acidic natural polymer known to date. It consists of a major 1,4-linked disaccharide repeating unit of D-uronic acid 1,4-β-D-glucosamine, and has an average of four negative charges (three sulfate groups and one carboxylate group) per monosaccharide unit. Heparin is both polydisperse, having an average molecular weight between 3,000 and 45,000 daltons, and heterogenous due to partial epimerization of D-glucuronic acid to L-iduronic acid and incomplete N- and O- sulfation, as reported by Kusche et al., *Proc. Natl. Acad. Sci.,* 77:6551–6555 (1980) and Comper, *Polymer Monograph* 7, 1981.

In addition, proteoglycans like heparin have a wide range of biological influences, including in blood chemistry, growth factor interaction and wound healing, interaction with basic structural proteins in the extracellular matrix and in cellular mediated immune responses. The basic nature of protein/peptide—heparin/complex carbohydrate interaction is important. Although heparin seems fairly heterogenous, it is now quite clear that different heparin fractions exhibit distinct and unique properties indicating some compositional and possibly structural specificity for its biological role, as reviewed by Cardin, A. D. and H. J. R. Weintraub, *Arteriosclerosis* 9, 21–32 (1989).

Heparinase, also referred to as heparin lyase, is the only known enzyme capable of degrading heparin that has been extensively characterized. It has been designated EC 4.2.2.7 by the Enzyme Commission. According to Galliher, et al., *Eur. J. Appl. Microbiol.* 15:252 (1982), the enzyme is a polysaccharide lyase found in the periplasmic space of *Flavobacterium heparinum,* a Gram-negative soil isolate. *F. heparinum* utilizes heparin as its sole source of carbon and nitrogen, as described by Hoving and Linker, *J. Biol. Chem.* 245:6170 (1970). Heparinase is the initial enzyme of heparin catabolism. Although constitutively expressed in low amounts, Galliher, et al., *App. Environ. Microbiol.* 41:360 (1981), have discovered that enzyme expression is induced by heparin and reversibly repressed by sulfate in the medium. Lindhardt, et al., *Appl. Biochem. Biotechnol.* 9:41 (1984), have shown that heparinase is inhibited by other polyanionic polysaccharides.

Heparinase has been purified by standard chromatographic techniques and its enzymatic properties characterized extensively, as described by scientists including Yang, et al., *J. Biol. Chem.* 260:1849 (1985). The enzyme is a 44,000 dalton monomeric protein with a pI of approximately 9.

Heparinase acts as an eliminase, leaving behind an unsaturated double bond at the non-reducing end group. This double bond is exploited in an assay for heparinase activity by the absorbance of the unsaturated product at 232 nm. The enzyme is marginally tolerant to salts and is very specific for heparin, having a $k_d$ of 30 nM. Heparinase has an activation energy of 4.5 kcal/mol, a km of 8×10−6 and a Vmax of 4×10−7 M/min.

Heparin is often used in surgery to prevent blood clotting and to increase the compatibility of extracorporeal devices such as heart-lung and kidney dialysis machines. The enzymatic degradation of heparin by heparinase is sufficient to eliminate the anticoagulation properties of heparin in surgery. As described by Langer, et al. in *Biomaterials: Interfacial Phenomenon and Applications, Adv. in Chem. Symposium Series,* Chap. 13, pp. 493–509 (1982), this property has led to the use of heparinase as an immobilized bioreactor in conjunction with heart-lung or kidney dialysis machines to deheparinize blood. Commercial application of the heparinase bioreactor is pending clinical trials.

A principal problem in the use of the heparinase bioreactor is the availability of sufficient amounts of pure heparinase to be immobilized onto a surface. This is primarily because the amount of heparinase constitutively expressed in *F. heparinum* is very low. Inducing expression of heparinase in *F. heparinum* with heparin is very expensive due to the amounts of heparin needed and the size of the fermentation to produce reasonable amounts of heparinase for any practical applications.

Cloning and expression of the heparinase gene is important in several ways. First, the only enzyme cloned and characterized to date which acts to depolymerise proteoglycans is heparinase. Second, heparin is the only anticoagulant commonly used in surgery so deheparinizing blood is an important medical problem. Moreover, heparinase catalyzed degradation of heparin into lower molecular weight heparin molecules can be used to yield products with specific anticoagulant activity, as discussed by Rosenfeld and Danishefsky, *Biochem. J.* 237:639–646 (1986).

Designing recombinant heparinases with altered activitie(s) would be interesting academically, as well as commercially. For example, heparinase can be used to deheparinize blood because the enzyme cleaves right at the AT-III binding oligomer. On the other hand, by further understanding the mechanism of the enzyme binding and depolymerizing heparin, recombinant heparinases with altered specificity could be designed, i.e. an AT-III binding heparin fragment not cleaved by the recombinant enzyme. This would be a very useful way of generating an AT-III binding heparin oligosaccharide, which currently is not available in large amounts, for use as an anticoagulant. Producing heparinases which could help and or improve in the enzyme purification or immobilization would also be quite valuable. For example, a tag (a particular peptide sequence) could be added at a region which does not alter the activity of the enzyme but makes the immobilization chemistry very efficient. This would help in improving enzyme loading onto the immobilization matrix.

It is therefore an object of the present invention to provide the gene encoding heparinase and a system for expression to facilitate the production of large amounts of heparinase.

It is another object of the present invention to provide methods and means for modifying the gene to produce recombinant heparinases having altered specificity and other desirable properties.

It is another object of the present invention to provide pure heparinase for use in the area of cytokine-proteoglycan interactions, as a tool or diagnostic as exemplified by fibroblast growth factor—heparin interactions.

SUMMARY OF THE INVENTION

The cloning of the heparinase gene from *Flavobacterium Heparinum* using the polymerase chain reaction is described. Two degenerate oligonucleotides, based on amino acid sequence derived from tryptic peptides of purified heparinase were used in the PCR with Flavobacterium genomic DNA as the template to generate a 600 base pairs probe. This probe was used to screen a pUC 18 Flavobacterium genomic library. The Open Reading Frame (ORF) corresponded to 1152 base pairs encoding a precursor protein of MW 43,800 daltons. Eleven different tryptic peptides (approximately 48% of the total amino acids) mapped into the ORF. The amino acid sequence reveals a 20-residue leader peptide.

Heparinase can be expressed from the gene. Additionally, the gene can be modified to produce heparinase with altered enzymatic activity, specificity, or binding properties. The sequence can also be used as a probe in the isolation of genes encoding other related enzymes.

DETAILED DESCRIPTION OF THE INVENTION

The gene encoding heparinase in *F. heparinum* has been cloned, wherein the coding and non-coding sequences are set forth in Sequence ID No. 1. The nucleotide and amino acid sequences are shown below:

The following sequence encodes a leader peptide, shown at positions 1 through 172 in Sequence ID No. 1:

```
CCTTT TGGGA GCAAA GGCAG AACCA TCTCC GAACA AAGGC AGAAC CAGCC TGTAA

ACAGA CAGCA ATTCA TCCGC TTTCA ACCAA AGTGA AAGCA TTTAA TACAA TACCA

GAATG TCGCA TTTCC CTTTC AGCGT ACTTT TTGGG TAAAT AACCA ATAAA AACTA

AAGAC GG
```

The following sequence encodes the heparinase, shown at positions 173 through 1327 of Sequence ID No. 1:

```
ATG AAA AAA CAA ATT CTA TAT CTG ATT GTA CTT CAG CAA CTG TTC CTC

TGT TCG GCT TAC GCC CAG CAA AAA AAA TCC GGT AAC ATC CCT TAC CGG

GTA AAT GTG CAG GCC GAC AGT GCT AAG CAG AAG GCG ATT ATT GAC AAC

AAA TGG GTG GCA GTA GGC ATC AAT AAA CCT TAT GCA TTA CAA TAT GAC

GAT AAA CTG CGC TTT AAT GGA AAA CCA TCC TAT CGC TTT GAG CTT AAA

GCC GAA GAC AAT TCG CTT GAA GGT TAT GCT GCA GGA GAA ACA AAG GGC

CGT ACA GAA TTG TCG TAC AGC TAT GCA ACC ACC AAT GAT TTT AAG AAA

TTT CCC CCA AGC GTA TAC CAA AAT GCG CAA AAG CTA AAA ACC GTT TAT

CAT TAC GGC AAA GGG ATT TGT GAA CAG GGG AGC TCC CGC AGC TAT ACC

TTT TCA GTG TAC ATA CCC TCC TCC TTC CCC GAC AAT GCG ACT ACT ATT

TTT GCC CAA TGG CAT GGT GCA CCC AGC AGA ACG CTT GTA GCT ACA CCA

GAG GGA GAA ATT AAA ACA CTG AGC ATA GAA GAG TTT TTG GCC TTA TAC

GAC CGC ATG ATC TTC AAA AAA AAT ATC GCC CAT GAT AAA GTT GAA AAA
```

-continued

```
AAA GAT AAG GAC GGA AAA ATT ACT TAT GTA GCC GGA AAG CCA AAT GGC

TGG AAG GTA GAA CAA GGT GGT TAT CCC ACG CTG GCC TTT GGT TTT TCT

AAA GGG TAT TTT TAC ATC AAG GCA AAC TCC GAC CGG CAG TGG CTT ACC

GAC AAA GCC GAC CGT AAC AAT GCC AAT CCC GAG AAT AGT GAA GTA ATG

AAG CCC TAT TCC TCG GAA TAC AAA ACT TCA ACC ATT GCC TAT AAA ATG

CCC TTT GCC CAG TTC CCT AAA GAT TGC TGG ATT ACT TTT GAT GTC GCC

ATA GAC TGG ACG AAA TAT GGA AAA GAG GCC AAT ACA ATT TTG AAA CCC

GGT AAG CTG GAT GTG ATG ATG ACT TAT ACC AAG AAT AAG AAA CCA CAA

AAA GCG CAT ATC GTA AAC CAG CAG GAA ATC CTG ATC GGA CGT AAC GAT

GAC GAT GGC TAT TAC TTC AAA TTT GGA ATT TAC AGG GTC GGT AAC AGC

ACG GTC CCG GTT ACT TAT AAC CTG AGC GGG TAC AGC GAA ACT GCC AGA

TAG (stop codon)
```

The following is the amino acid sequence of heparinase, set forth in Sequence ID No. 2:

```
Met Lys Lys Gln Ile Leu Tyr Leu Ile Val Leu Gln Gln Leu Phe Leu

Cys Ser Ala Tyr Ala Gln Gln Lys Lys Ser Gly Asn Ile Pro Tyr Arg

Val Asn Val Gln Ala Asp Ser Ala Lys Gln Lys Ala Ile Ile Asp Asn

Lys Trp Val Ala Val Gly Ile Asn Lys Pro Tyr Ala Leu Gln Tyr Asp

Asp Lys Leu Arg Phe Asn Gly Lys Pro Ser Tyr Arg Phe Glu Leu Lys

Ala Glu Asp Asn Ser Leu Glu Gly Tyr Ala Ala Gly Glu Thr Lys Gly

Arg Thr Glu Leu Ser Tyr Ser Tyr Ala Thr Thr Asn Asp Phe Lys Lys

Phe Pro Pro Ser Val Tyr Gln Asn Ala Gln Lys Leu Lys Thr Val Tyr

His Tyr Gly Lys Gly Ile Cys Glu Gln Gly Ser Ser Arg Ser Tyr Thr

Phe Ser Val Tyr Ile Pro Ser Ser Phe Pro Asp Asn Ala Thr Thr Ile

Phe Ala Gln Trp His Gly Ala Pro Ser Arg Thr Leu Val Arg Thr Pro

Glu Gly Glu Ile Lys Thr Leu Ser Ile Glu Glu Phe Leu Ala Leu Tyr

Asp Arg Met Ile Phe Lys Lys Asn Ile Ala His Asp Lys Val Glu Lys

Lys Asp Lys Asp Gly Lys Ile Thr Tyr Val Ala Gly Lys Pro Asn Gly
```

-continued

| | | | | | | | | | | | | | | |
|---|---|---|---|---|---|---|---|---|---|---|---|---|---|---|
| Trp | Lys | Val | Glu | Gln | Gly | Gly | Tyr | Pro | Thr | Leu | Ala | Phe | Gly | Phe | Ser |
| Lys | Gly | Tyr | Phe | Tyr | Ile | Lys | Ala | Asn | Ser | Asp | Arg | Gln | Trp | Leu | Thr |
| Asp | Lys | Ala | Asp | Arg | Asn | Asn | Ala | Asn | Pro | Glu | Asn | Ser | Glu | Val | Met |
| Lys | Pro | Tyr | Ser | Ser | Glu | Tyr | Lys | Thr | Ser | Thr | Ile | Ala | Tyr | Lys | Met |
| Pro | Phe | Ala | Gln | Phe | Pro | Lys | Asp | Cys | Trp | Ile | Thr | Phe | Asp | Val | Ala |
| Ile | Asp | Trp | Thr | Lys | Tyr | Gly | Lys | Glu | Ala | Asn | Thr | Ile | Leu | Lys | Pro |
| Gly | Lys | Leu | Asp | Val | Met | Met | Thr | Tyr | Thr | Lys | Asn | Lys | Lys | Pro | Gln |
| Lys | Ala | His | Ile | Val | Asn | Gln | Gln | Glu | Ile | Leu | Ile | Gly | Arg | Asn | Asp |
| Asp | Asp | Gly | Tyr | Tyr | Phe | Lys | Phe | Gly | Ile | Tyr | Arg | Val | Gly | Asn | Ser |
| Thr | Val | Pro | Val | Thr | Tyr | Asn | Leu | Ser | Gly | Tyr | Ser | Glu | Thr | Ala | Arg. |

EXAMPLE 1

Isolation and analysis of cDNA encoding heparinase in F. heparinum.

Because preliminary cloning attempts by others utilizing 1) antibody screening, 2) screening for functionally active heparinase in *E. coli* and 3) screening for the heparinase gene using probes derived from protein sequences regenerated by cyanogen bromine (CNBr) chemical digest were unsuccessful, the polymerase chain reaction was used to clone the heparinase gene. The reverse phase purified heparinase was reduced, alkylated and digested with trypsin to obtain approximately 60 peptide peaks which were separated and collected by reverse phase HPLC monitored at 210 nm and at 277 nm (for tyrosine and tryptophan), as described below.

Tryptic Digest and Protein Sequence Analyses

Heparinase was purified as described by Dietrich et al., *J. Biol. Chem.* 248:6408 (1973), Otatani et al., *Carbohyd. Res.* 88:291 (1981), and Yang et al., *J. Biol. Chem.* 260:1849 (1985), which are incorporated by reference herein. A final purification step was carried out by High Performance Liquid Chromatography (HPLC) using a reverse phase column that exploits the hydrophobic residues of the protein.

A nanomole (approximately 45 μg) of the purified enzyme was denatured in 50 μl of an 8M urea, 0.4M ammonium carbonate solution, reduced with 5 mM dithiothreitol (DTT) at 50° C., cooled to room temperature, and alkylated with 10 mM iodoacetamide for 15 minutes in the dark. The total reaction volume was 200 μl. To this reaction mixture, ½₅th w/w of trypsin was added and digestion carried out at 37° C. for 24 hour. The reaction was terminated by heating the sample at 65° C. for 2 minutes. The digest was separated by reverse phase HPLC using a gradient of 0 to 80% acetonitrile. The tryptic peptides were monitored at 210 and 277 nm.

The tryptic peaks were collected in Eppendorff tubes. Based on the homogeneity of the peptide peak, eight different peaks were sequenced using an Applied Biosystems sequencer, model 477, with an on-line model 120 PTH amino acid analyzer located in the Biopolymers lab, Center for Cancer Research, MIT. The sequences are set forth in Table I below. The designation (K,R) is used in Table I to indicate that trypsin cuts at either lysine or arginine residues. The asterisks in Table I represent amino acids that could not be determined. The peptide designated td Lx is the longest peptide sequenced having 38 residues. Native undigested heparinase was also sequenced to determined the N-terminus amino acids.

TABLE I

Sequences of Tryptic Peptides of Heparinase

| Peptide | Amino Acid Sequence |
|---|---|
| td 04, Sequence ID NO. 3 | (K, R) G I C E Q G S S R |
| td 09, Sequence ID NO. 4 | (K, R) T V Y H Y G K |
| td 09, Sequence ID NO. 5 | (K, R) T S T I A Y K |
| td 21, Sequence ID NO. 6 | (K, R) F G I Y R |

TABLE I-continued

Sequences of Tryptic Peptides of Heparinase

| Peptide | Amino Acid Sequence |
|---|---|
| td 33, Sequence ID NO. 7 | (K, R) A D I V N Q Q E I L I G R D D * G Y Y F K |
| td 39, Sequence ID NO. 8 | (K, R) I T Y V A G K P N G N K V E Q G G Y P T L A F * |
| td 43, Sequence ID NO. 9 | (K, R) M P F A Q F P K D C WI T F D V A I D * T K |
| td 40, Sequence ID NO. 10 | (K, R) N L S G Y S E T A R |
| tdm4, Sequence ID NO. 11 | K N I A H D K V E K K |
| td 72, Sequence ID NO. 12 | K T L S I E E F L A L Y D R |
| td Lx, Sequence ID NO. 13 | R S Y T F S V Y I P S S F P D N A T T I F A Q W H G A P S R T L V T P E I K |

Three sets of primers were designed and synthesized, as shown in Table II. Primers were synthesized with an Applied Biosystems sequencer, model 477, with an on-line model 120 PTH amino acid analyzer located in the Biopolymers lab, Center for Cancer Research, MIT. These primer sets were used in the PCR amplification system for cloning the heparinase gene. The symbol "I" represents the nucleotide inosine. The amino acids of each peptide, depicted in boldface type, represent the residues chosen for the primer design. Two different sets of primers were constructed for tryptic peptide 33 to reduce the degree of inosine substitution at the 3' end of the primer.

TABLE II

Heparinase Primer Design

Peptide: td 04 Sequence ID NO. 3

Amino Acid Sequence:

K G I C E Q G S S R primers:

$y^1$, Sequence ID NO. 14   5'- AAA  GGI   AT(T/C/A)  TG(T/C)  GA(A/G)  CA(A/G)  GG  -3'

$y^2$                       3'- CC  (C/T)TG  (C/T)TC  (G/A)CA  (T/G/A)AT  I CC  TTT  -5'

Peptide: td 43

Amino Acid Sequence:

(K, R) M P F A Q F P K D E WI T F C V                   A I D * T K primers:

D Sequence ID NO. 15  5'- ATG  CCI  TT(T/C)  GCI  CA(A/G)  TT(T/C)  CCI  AA(A/G)  GA(T/C)  GA  -3'

E                     3'- TAC  GGI  AA(A/G)  CGI  GT(T/C)  AA(A/G)  GGI  TT(T/C)  CT(A/G)  CT  -5'

Peptide: td 33

Amino Acid Sequence:

(K, R) A D I V Q Q E I L I G R D D * G Y Y F K A

TABLE II-continued

Heparinase Primer Design primers:

A, Sequence ID NO. 16   5'-  ATI   AA(T/C)   CA(A/G)   GA(A/G)ATI   (C/T)TI   AT(T/C/A)   GG  -3'

B                       3'-  CCI ATI A(G/A)   I AT   (T/C)TC   (T/C)TG   (A/G)TT   I CA   (A/C)AT

C                       3'-  CCI ATI A(G/A)   I AT   (T/C)TC   (T/CTG   (A/G)TT   I CA   (T/G)AT  -5'

Of the six RHPLC peaks initially sequenced (Table I), three were chosen for primer design. Three sets of primers were designed (Table II). The PCR product of the combination the primers td43 and td33 was about 150 base pairs in length. The combination of td4 and td33 primers were about 600 base pairs. Primer td43 was 5' to primer td33 and primer td4 was 5' to td43 primer. Using the PCR product of td4 and td33 as a template and td43 and td4 as primers the predicted 150 base pair product was obtained confirming that td43 was between td4 and td33.

Figure 1:
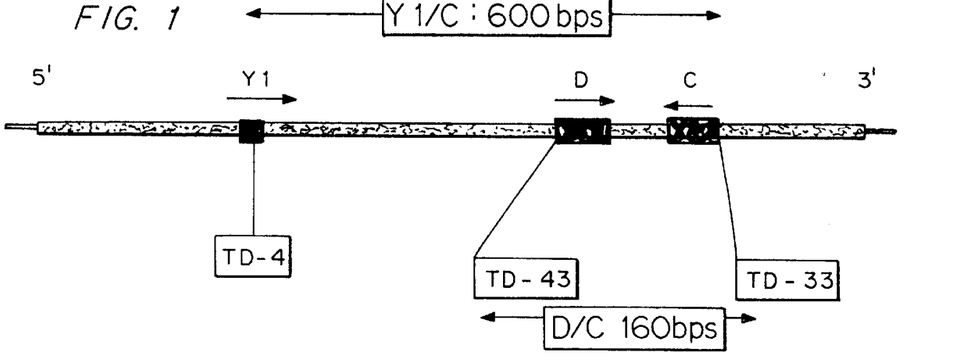
FIG. 1 is a schematic representation of the PCR products Y1:C and D:C which are 600 and 160 basepairs, respectively. The 600 basepair PCR product was used as a template with D and C as primers to generate the 160 basepair D:C product.

The 600 basepair product shown in FIG. 1 represents about 51% of the approximated total 1170 base pairs for the heparinase gene, assuming 43,000 dalton for heparinase and a 110 dalton average amino acid with a molecular weight corresponding to about 390 amino acids times three which is 1170 bases.

The 600 base pair probe was chosen for screening a pUC 18 library by high stringency colony hybridization. Two positive clones were identified which were carried through for three rounds of colony purification.

Genomic DNA, RNA, and Plasmid Library

The *F. heparinum* genomic DNA was isolated by the A.S.A.P.™ kit (Boehringer Mannheim, Indianapolis, Ind.) with the following modifications. The DNA was desalted over a Sephadex™ G-50 column (Nick column, Pharmacia, Piscataway, N.J.) and concentrated using a Centricon™ P-30 (Amicon Division, Beverly, Mass.) to a final volume of 100 l. From $1 \times 10^9$ cells, 105–115 g of DNA typically were obtained. Total cellular mRNA was isolated using the guanidine thiocyanate procedure set forth in the Promega technical information publication TB 087 12/89, Promega Corp. Madison, Wis. 53711. A pUC 18 plasmid was obtained from Dr. A. J. Sinskey, of the Department of Biology at the Massachusetts Institute of Technology. The library was constructed using the *F. heparinum* genomic DNA. The genomic DNA was sonicated and modified by adding EcoRI linkers and then ligated to the pUC 18 vector. DH5a was transformed with the pUC 18 genomic library.

Amplification of the PCR Product

Amplification of the heparinase tryptic digest primers was carried out in a 25 l reaction volume containing 50 mM KCl, 10 mM Tris HCl (pH 8.3), 1.5 mM $MgCl_2$ and 0.01% gelatin plus the four deoxyribose nucleotide triphosphates(dNTPs) at 200M, using 0.5M primer and 3 l of the genomic DNA as the template, 2.5 units of the Taq polymerase (Cetus Corp., Emeryville, Calif.) and 25 l of mineral oil. The samples were placed on an automated heating block (DNA thermal cycler, Perkin Elmer Corp., Norwalk, Conn.) programmed for step cycles of temperatures 92° C. (2 minutes), 50° C. (1 minute) and 72° C. (3 minutes). This cycle was repeated 35 times. The final cycle had a 72° C. 10 minute extension. The PCR products were analysed on a 0.8% agarose gel containing 0.6 μg/ml ethidium bromide. The control reaction was provided by the Cetus kit.

Screening of the *Flavobacterium heparinum* pUC 18 genomic library

The pUC 18 library was titered to give approximately 1500 colonies to be tested by the probe generated by PCR. Each plate had approximately 100 colonies which were grown directly on nitrocellulose, to an appropriate small size, and then duplicated to be grown further overnight.

The PCR probe was labelled using the Random Hexanucleotide™ kit (RHN) (IBI Biochemicals Ltd.) which is described briefly as follows. One microgram DNA from the PCR product run was isolated from a low melt agarose gel, denatured by boiling at 95° C. for 10 minutes, and then chilled on ice. To the denatured DNA were added 10 mM dNTPs (dATP, dGTP, dCTP, dTTP), random hexanucleotides in the reaction buffer, and 50 μCi of $^{32}$PdCTP(3000 Ci/mmole). The reaction was carried with Klenow for 30 minutes at 37° C. and terminated using 0.2M EDTA. Following the labelling reaction, the labelled probe was purified from the free nucleotide by using a Sephadex G-50 column (Nick Column, Pharmacia, Piscataway, N.J.)

The colonies were screened with the labelled probe using standard colony hybridization procedures as described by Maniatis et al., *Molecular Cloning: A Laboratory Manual,* Cold Spring Harbor Laboratory, Cold Spring Harbor, N.Y., incorporated herein by reference.

Figure 2:
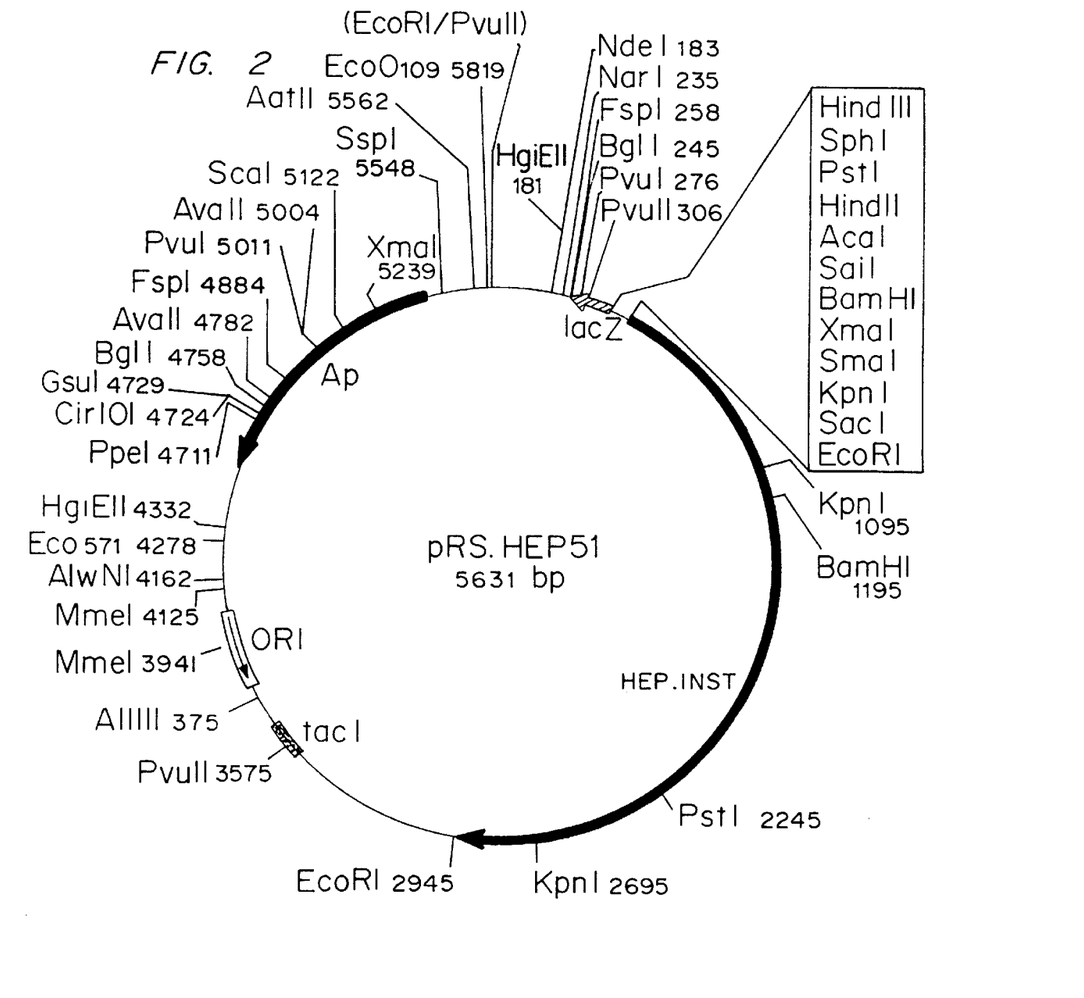
FIG. 2 is the restriction map of the genomic DNA pUC 18 plasmid, pRS.HEP51, having an insert containing the heparinase gene. The plasmid is 5631 bases long and has approximately 2300 bases of insert. The heparinase gene is in the KpnI—KpnI fragment.
Figure 3:
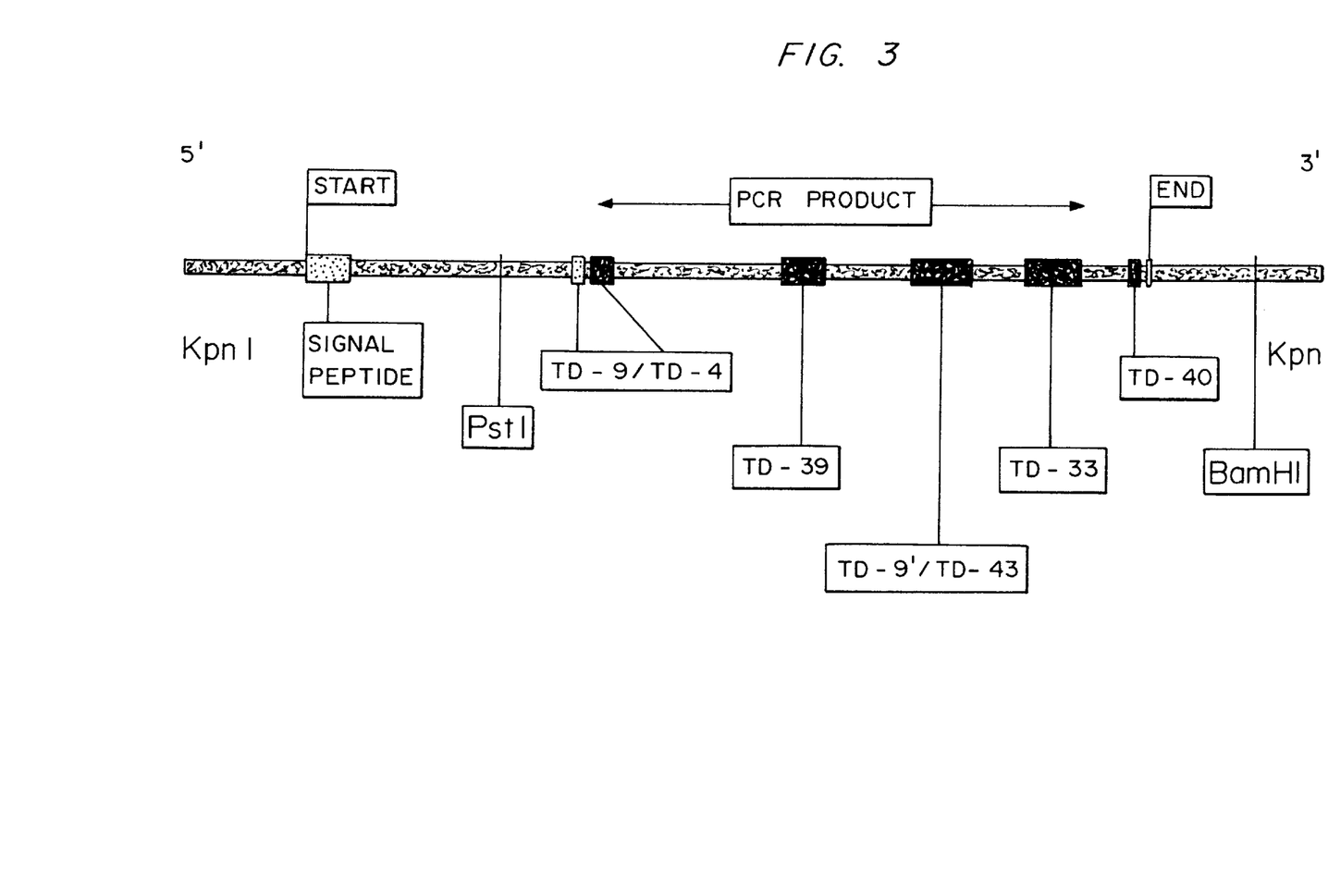
FIG. 3 is a KpnI—KpnI fragment map showing the heparinase gene structure with the different tryptic peptides mapping into the open reading frame. Six different peptides mapped into the heparinase gene translation region.

Two positive clones were isolated and the plasmids tested for their ability to generate the 600 basepair PCR product. Both of the clones tested positive and were further characterized by restriction mapping. Clone pRS Hep 51 is a 2.3 kb insert in pUC 18 (shown in FIG. 2) with a Kpn—Kpn fragment of about 1.6 kb. This fragment was a positive template for generating a 600 basepair PCR product. The KpnI—KpnI fragment of pRS 51 was subcloned into M13 and sequenced.

DNA Sequencing

DNA sequencing was performed using phage M13 and employing the dideoxyadenosine 5'-alpha-$^{35}$S-triphosphate and Sequenase (US Biochemical Corp, Cleveland, Ohio) as described by the manufacturer. The sequence data was obtained using successive nested deletions in M13 using T4 DNA polymerase as per Cyclone I Biosystems (International Biotechnologies Inc., New Haven, Conn.) or sequenced using synthetic oligonucleotide primers.

The sequence reveals a single, continuous open reading frame (ORF) of 1152 basepairs corresponding to 384 amino acids and a leader sequence of about 21 amino acids. The PCR product spans from 566 to 1216 bases from the start site and corresponds to about 57% of the total gene.

Initially six different tryptic peptides mapped into the ORF. Subsequently, five other peptides were sequenced for structural studies and all of them mapped into the ORF, for a total of about 48% of the total 367 amino acids. There are three cysteines in all, one associated with the signal peptide. The signal peptide is typical of prokaryotic sequences, having a charged N-terminal region, a core hydrophobic region and a cleavage region with a standard Ala.xxx.Ala site for cleavage.

EXAMPLE 2

Expression of the heparinase gene in *E. coli*.

Two different expression systems were selected for the expression of heparinase in *E. coli:* the Omp A expression system and the pKK hyper-expression system. The plasmid designs for both expression systems are shown in Table III.

Omp A expression system

The Omp A expression system secretes the protein of interest into the periplasmic space, as directed by the Omp A signal sequence, described by Ghrayeb, et al., *EMBO J.* 3:2437 (1984), incorporated herein by reference. This system was chosen since heparinase is naturally expressed into the periplasmic space of *F. heparinum*. The plasmid is under the control of the lac repressor and is induced by the addition of IPTG (isopropyl-β-D thiogalactoside) to the medium. The plasmid was inserted in the pIN-III omp A-3 vector.

The heparinase insert was generated by PCR utilizing the N terminal and the C terminal sequences of heparinase with two appropriate restriction sites suitable for cloning into the EcoRI-BamHI sites. Two primers were constructed as shown in Table II. The insert was amplified by 5 cycles of PCR and ligated to the Omp A pIN vector with the *E. coli* periplasmic leader sequence. DH5α was transformed and expression was induced with 1 mM IPTG for 3–5 hours.

As shown in Table III, the construct of the Omp A expression system results in two extra amino acids at the amino terminal of the heparinase gene, Gly and Ile. The heparinase sequence begins with a Gln.

The pKK expression system

The pKK expression system is used for over-expression of proteins in accordance with the methods of Brosius and Holy, *Proc. Natl. Acad. Sci.,* 81:6929 (1984) and Jaffe et al., *Biochem.* 27:1869 (1988), incorporated by reference herein. This system contains a strong tac promoter which, in appropriate hosts, is regulated by the lac repressor and induced by the addition of IPTG, as in the Omp A system. The plasmid pKK223-3 has a pUC 8 multiple cloning site and a strong rrnB ribosomal terminator immediately following the tac promotor. The ribosomal binding site of the plasmid was utilized by cloning the heparinase gene into a SmaI site, which is about 12 bases from the start codon ATG. Like the Omp A construction, the heparinase insert is obtained by PCR with SmaI and HindIII restriction sites at the N and the C terminals of the protein. As shown in Table III, the native heparinase leader sequence was used for over-production into the periplasm.

Periplasmic proteins of *E. coli* were isolated by osmotic shock. Briefly, 1.5 ml of cells were centrifuged after induction and washed with 10 mM Tris pH 7.5. The cells were then suspended in 20% sucrose in 10 mM Tris pH 7.5 and 5 Al of 0.5M EDTA. After a five minute incubation on ice, the cells were centrifuged and osmotically shocked by adding approximately 150 μl water. The periplasmic extract was used to determine enzyme activity. Heparinase activity was determined by monitoring the wavelength at 232 nm and by the Azure A methods of Bernstein et al., *Methods of Immunology* 137:515 (1988), incorporated herein by reference.

The periplasmic extracts were analyzed by sodium dodecyl sulfate-polyacrylamide gel electrophoresis (SDS-PAGE) using the method of Laemmli, *Nature* 227:690 (1974) and stained using Coumassie blue. In addition, a Western blot assay was performed to confirm the presence of heparinase using a heparinase monoclonal antibody. Heparinase was electrophoretically transferred from the SDS-PAGE gel onto nitrocellulose using the method of Gershoni and Palade, *Analytical Biochem.* 131:1 (1983), and then incubated with the monoclonal antibody. This antibody was stained using a secondary antibody conjugated to horseradish peroxidase.

TABLE III

Design of OmpA and pKK plasmids for Expression of Recombinant Heparinase in *E. coli*

Omp A secretion Expression system

| N | | Gly | Ile | Gln | Lys | (Sequence ID NO. 17) | | | | | | Thr | Ala | Arg | End | | C |
|---|---|---|---|---|---|---|---|---|---|---|---|---|---|---|---|---|---|
| XXX | GGA | ATT | CAG | AAA | (Sequence ID NO. 18) | – | – | – | – | – | – | – | – | ACT | GCC | AGA | TAG | GGATCC | (Sequence ID NO. 19) | XXX |
| XXX | CCT | TAA | GTC | TTT | | – | – | – | – | – | – | – | – | TGA | CGG | ACT | ATC | CCTAGG | | XXX |
| | EcoRI | | | | | | | | | | | | | | | | Bam HI | pKK over-Expression system

TABLE III-continued

Design of OmpA and pKK plasmids for Expression of Recombinant Heparinase in *E. coli*

| N | Met | Lys | Lys | | | | | Ala | Arg | End | | C |
|---|---|---|---|---|---|---|---|---|---|---|---|---|
| XXX | TAA | CCC | GGG | ATG | AAA | AAA | (Sequence ID NO. 20) | ----- | GCC | AGA | TAG | AAG CTT CCG (Sequence ID NO. 21) XXX |
| XXX | ATT | GGC | CCC | TAC | TTT | TTT | | ----- | CGG | TCT | ATC | TTC GAA GGC XXX |
| | | Sma I | | | | | | | | | | Hind III |

RNA Dot Blot Assay

The total cellular RNA was immobilized onto a Zeta probe™ membrane (Biorad, Richmond, Calif.) by alkaline RNA denaturation and fixation, and probed using the 600 base PCR product, used in screening for the heparinase gene. The hybridization was carried out with dot blot apparatus in accordance with the method of Thomas, *Proc. Natl. Acad Sci.* 77:5201 (1980). The RNA signal under different growth conditions has been investigated by Galliher, et al., *Eur. J. Appl. Microbiol.* (1982). It was established by those studies that heparinase at the protein level is optimally expressed under low sulphur conditions, which removes the requirement of heparin for induction. Heparinase mRNA signal under low sulphur growth conditions was therefore studied with and without heparin induction.

Both the OmpA and the pKK systems expressed heparinase. The OmpA system did not efficiently transport heparinase to the periplasm. For reasons not known, a large fraction of recombinant heparinase was retained in the cytoplasmic region along with the Omp A signal sequence. At lower temperatures (25°–30° C.) of growth, there was some secretion into the periplasmic space.

The pKK overproduction system produced heparinase only in the periplasmic space. The pKK system used the native *F. heparinum* heparinase leader sequence in which there was no problem with the transport of the recombinant protein with a foreign leader sequence. The pKK system expressed heparinase without any aberrant processing, although the expression was again optimal at lower temperatures. The presence of heparinase in the periplasm was confirmed by western blotting and by comparing in situ tryptic digest of the recombinant heparinase with that of the native heparinase, in terms of the peak profiles and some peaks which were isolated and sequenced.

A positive signal was obtained for the isolated *F. heparinum* mRNA using the 600 basepair probe derived from the PCR which has been used for isolating the heparinase gene, confirming that the gene isolated was a *F. heparinum* gene cloned in *E. coli*.

The expressed heparinase appeared to have at least some heparinase activity.

The sequence can be modified to alter specific enzymatic activity or binding specificity or affinity by substitution of one or more amino acids, using site directed mutagenesis or substitution of oligomers into the sequence encoding the heparinase. Methods and materials to accomplish this are known to those skilled in the art. The modified gene is then expressed and the product routinely screened for the altered activity.

Although described with reference to two specific expression systems, other expression systems are well known and commercially available. The heparinase gene can be expressed in these systems, using similar vectors and signal peptides or leader sequences.

Modifications and variations of the present invention will be obvious to those skilled in the art. Such modifications and variations are intended to come within the scope of the following claims.

---

We claim:

1. A method for obtaining a nucleic acid molecule encoding a modified heparinase I from *Flavobacterium heparinum* comprising mutating a nucleic acid molecule encoding the sequence in SEQ ID No. 2, expressing the mutated sequence in an appropriate host, and screening the expressed heparinase for enzymatic activity.

2. The method of claim 1 further comprising screening the heparinase expressed from the mutated nucleic acid molecule for modified binding activity.

3. The method of claim 1 further comprising screening for increased specific activity.

* * * * *